(12) United States Patent
Tuvim

(10) Patent No.: US 6,387,256 B1
(45) Date of Patent: May 14, 2002

(54) CHROMATOGRAPHY COLUMN

(75) Inventor: Yuri Tuvim, Newton, MA (US)

(73) Assignee: Waters Investments Limited

( * ) Notice: Subject to any disclaimer, the term of this patent is extended or adjusted under 35 U.S.C. 154(b) by 20 days.

(21) Appl. No.: 09/613,520

(22) Filed: Jul. 10, 2000

(51) Int. Cl.$^7$ .............................................. B01D 15/08
(52) U.S. Cl. ........................ 210/198.2; 210/656; 96/101
(58) Field of Search .............................. 210/656, 198.2, 210/232, 450; 96/101

(56) References Cited

U.S. PATENT DOCUMENTS

| | | | | |
|---|---|---|---|---|
| 3,440,864 A | | 4/1969 | Blume ..................... | 210/198.2 |
| 3,483,986 A | | 12/1969 | Wright ..................... | 210/198.2 |
| 4,636,315 A | * | 1/1987 | Allen ....................... | 210/198.2 |
| 4,655,917 A | * | 4/1987 | Shackelford ............. | 210/198.2 |
| 4,670,141 A | | 6/1987 | Shackelford et al. ..... | 210/198.2 |
| 4,719,011 A | * | 1/1988 | Shalon .................... | 210/198.2 |
| 4,732,687 A | * | 3/1988 | Muller ..................... | 210/198.2 |
| 4,752,391 A | * | 6/1988 | Porsch .................... | 210/198.2 |
| 4,755,293 A | * | 7/1988 | Sakamoto ................ | 210/198.2 |
| 4,797,209 A | * | 1/1989 | Jackson ................... | 210/198.2 |
| 4,806,238 A | * | 2/1989 | Sattler ..................... | 210/198.2 |
| 4,861,473 A | | 8/1989 | Shackelford et al. ..... | 210/198.2 |
| 4,876,005 A | * | 10/1989 | America ................... | 210/198.2 |
| 4,882,047 A | * | 11/1989 | Shalon .................... | 210/198.2 |
| 4,888,112 A | * | 12/1989 | Kronwald ................ | 210/198.2 |
| 4,894,152 A | * | 1/1990 | Colvin ..................... | 210/198.2 |
| 4,968,421 A | * | 11/1990 | Spacek .................... | 210/198.2 |
| 5,013,433 A | * | 5/1991 | Shalon .................... | 210/198.2 |
| 5,021,162 A | * | 6/1991 | Sakamoto ................ | 210/198.2 |
| 6,224,760 B1 | * | 5/2001 | Davies ..................... | 210/198.2 |

\* cited by examiner

*Primary Examiner*—Ernest G. Therkorn
(74) *Attorney, Agent, or Firm*—Brian Michaelis

(57) ABSTRACT

A chromatography column is disclosed. The large diameter chromatography column comprises a column body with threaded end portions. At each of the end portions, a respective filter housing is disposed. A respective threaded end cap is threaded onto each of the threaded end portions. Each of the end caps has holes for receiving a plurality of mechanical fasteners. The mechanical fasteners are installed into each end cap and apply pressure against the filter housing which forces the filter housing against the face of the column, thus sealing it. When the need to open the column arises, the mechanical fasteners can be easily loosened to release the tension on the thread between column body and end cap. After this, the end cap can be unscrewed with minimal torque.

11 Claims, 3 Drawing Sheets

CHROMATOGRAPHY COLUMN

FIELD OF THE INVENTION

The present invention relates to a chromatography column for use in liquid chromatography systems, and more particularly to large columns having a diameter greater than approximately 50 mm.

BACKGROUND OF THE INVENTION

A liquid chromatography system consists of the following major components: a pump, an injector, a column and a detector. Chromatographic separation occurs in the column when a solvent carrying a sample passes through porous media that is tightly packed in the column. This packed bed is retained in the column by filters that are being held by end caps. A poorly packed column, plugged filters, or a fouled bed will severely impair an analysis.

In general, there are two major designs of chromatographic columns. The first major design comprises a "small" diameter (up to 30 mm) column having a tubular body with threaded ends that are capped by end-fittings. The second major design, as shown in FIG. 1, comprises a "large" diameter column (50 mm and up) having a tubular body with flanges welded to the tubular body. End-caps are attached to the flanges by bolts. Because conventional large diameter chromatography columns are expensive and bulky, it would be advantageous to extend the threaded column design to large diameter columns.

Unfortunately, there is one significant obstacle to implementing the threaded design with large diameter columns. It is very difficult to open a large column that utilizes a threaded design, and columns need to be opened from time to time so blocked filters can be replaced or the column can be repacked.

To open a large diameter, threaded column, a wrench must be utilized to apply unscrewing torque to the end-fittings. The magnitude of the required torque is exponentially proportional to the diameter of the thread. The torque required to open large diameter, threaded columns is so great, they have not been practical to use.

SUMMARY OF THE INVENTION

The present invention provides a large diameter chromatography column having a threaded design that can be easily opened by applying very moderate torque.

According to the invention, a large diameter chromatography column comprises a column body with threaded end portions. At each of the end portions, a respective filter housing is disposed. An end cap is threaded onto each of the threaded end portions. Each of the end caps has holes for receiving a plurality of mechanical fasteners. The mechanical fasteners apply pressure on the filter housing which forces it against the face of the column. When the need to open the column arises, the mechanical fasteners can be easily loosened to release the tension on the thread between column body and end cap. After this, the end cap can be unscrewed by hand without using any tools. Thus, the novel chromatography column of the present invention can be opened with minimal effort.

An advantage of the chromatography column of the present invention is that it can be easily opened for repacking and/or changing filters.

Another advantage of the chromatography column of the present invention is that it is much less expensive to manufacture than the flanged column of the same diameter.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

Figure 1:
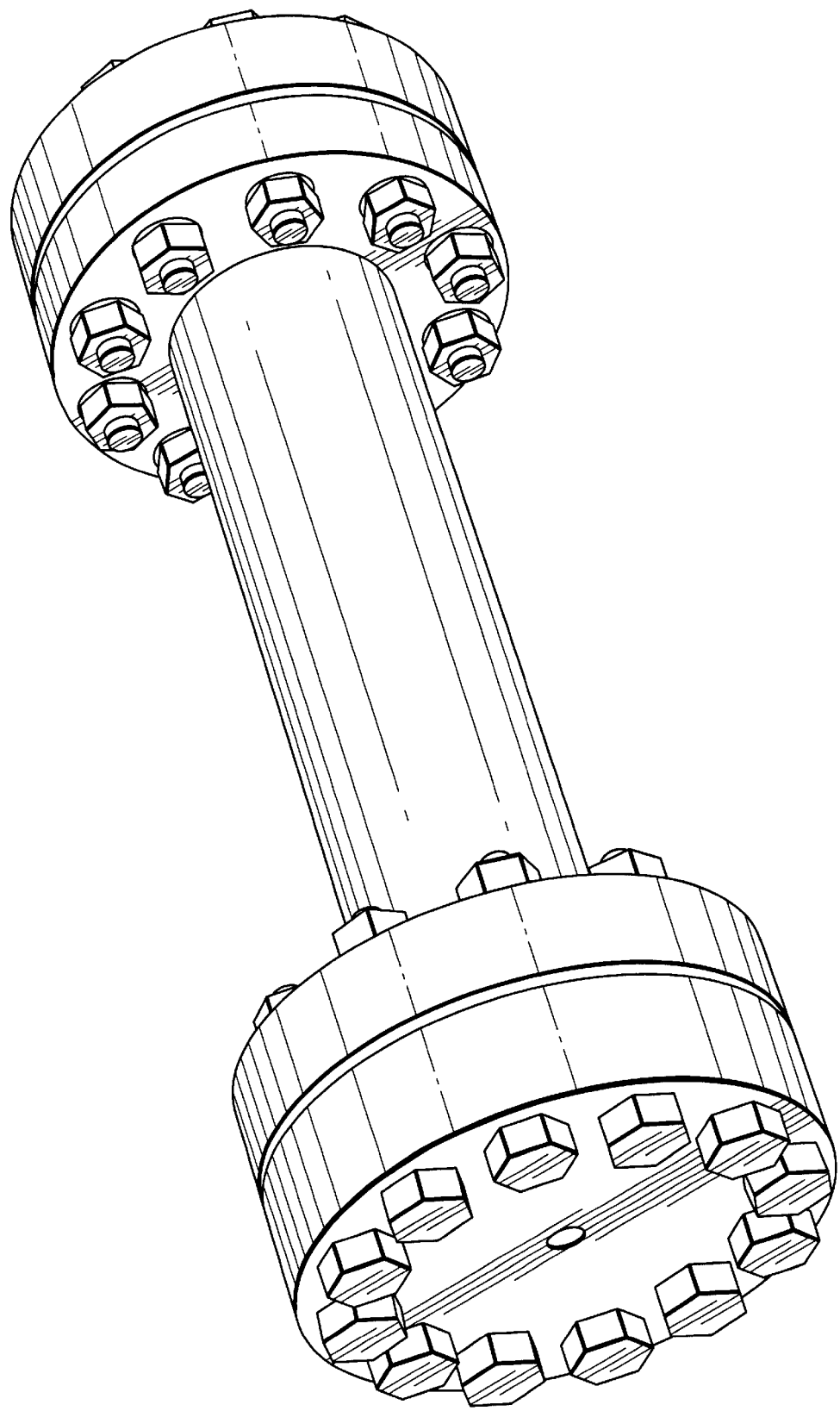
FIG. 1 illustrates a prior art flanged chromatography column.
Figure 2:
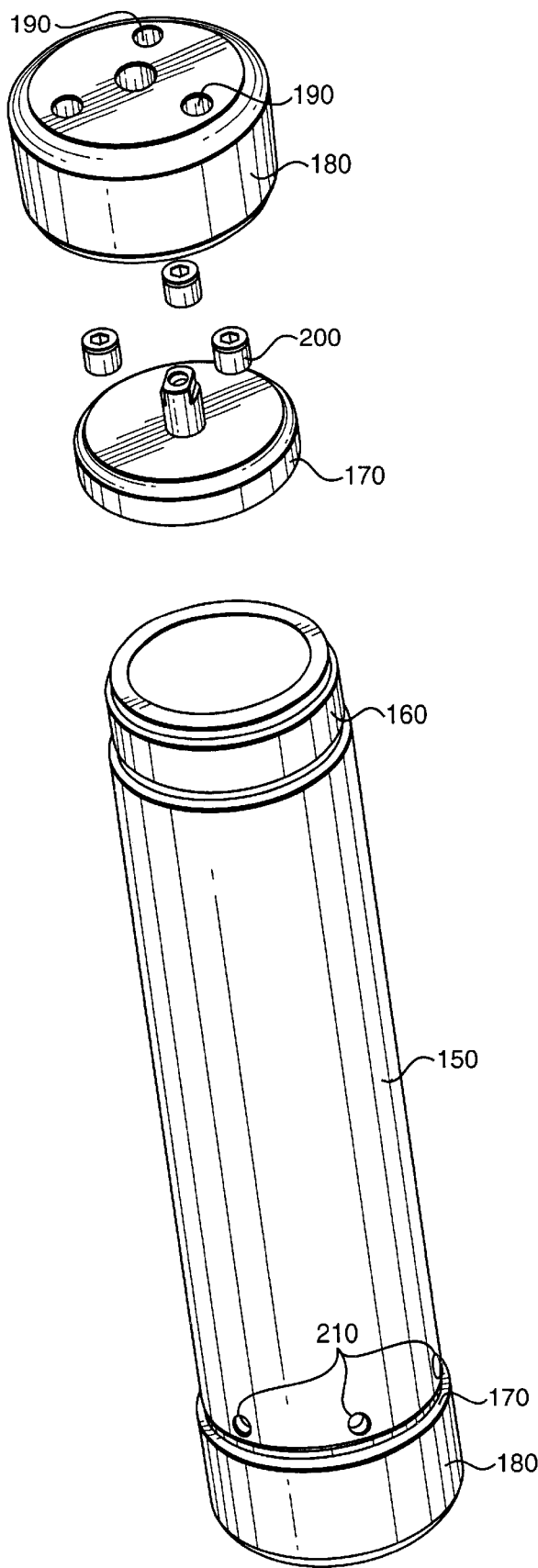
FIG. 2 is an exploded view of a chromatography column according to the present invention.

FIG. 2 shows a chromatography column according to the present invention. The chromatography column comprises a column body 150 including external threaded portions 160. Typically, the column body has a diameter of 50 mm or greater. The column body in this illustrative embodiment has an internal diameter of 50 mm and wall thickness of approximately 0.30".

The column according to the invention also comprises a filter housing 170 disposed at each end of the column body 150. The filter housing 170 includes a filter and distributor (not shown) for liquid to pass through.

The illustrative column further comprises two end caps 180. The end caps 180 have interior threads that screw on to the threaded portion 160 of the column body 150.

A plurality of small diameter holes 190 are disposed in the end caps 180. The holes in this illustrative embodiment are approximately ⅜" in diameter.

A plurality of mechanical fasteners 200 are configured to be screwed into the holes 190 in the end caps 180. When the filter housing 170 is disposed to the end of the column and the end caps are screwed on, the installed mechanical fasteners 200 are turned to press the filter housing 170 against the end of the column body 150 to effectively seal the chromatography column. In an illustrative embodiment of the present invention, three mechanical fasteners are used to press the filter housing 170 to the column body. Depending on the size of the chromatography column, three or more mechanical fasteners can be used.

Figure 3:
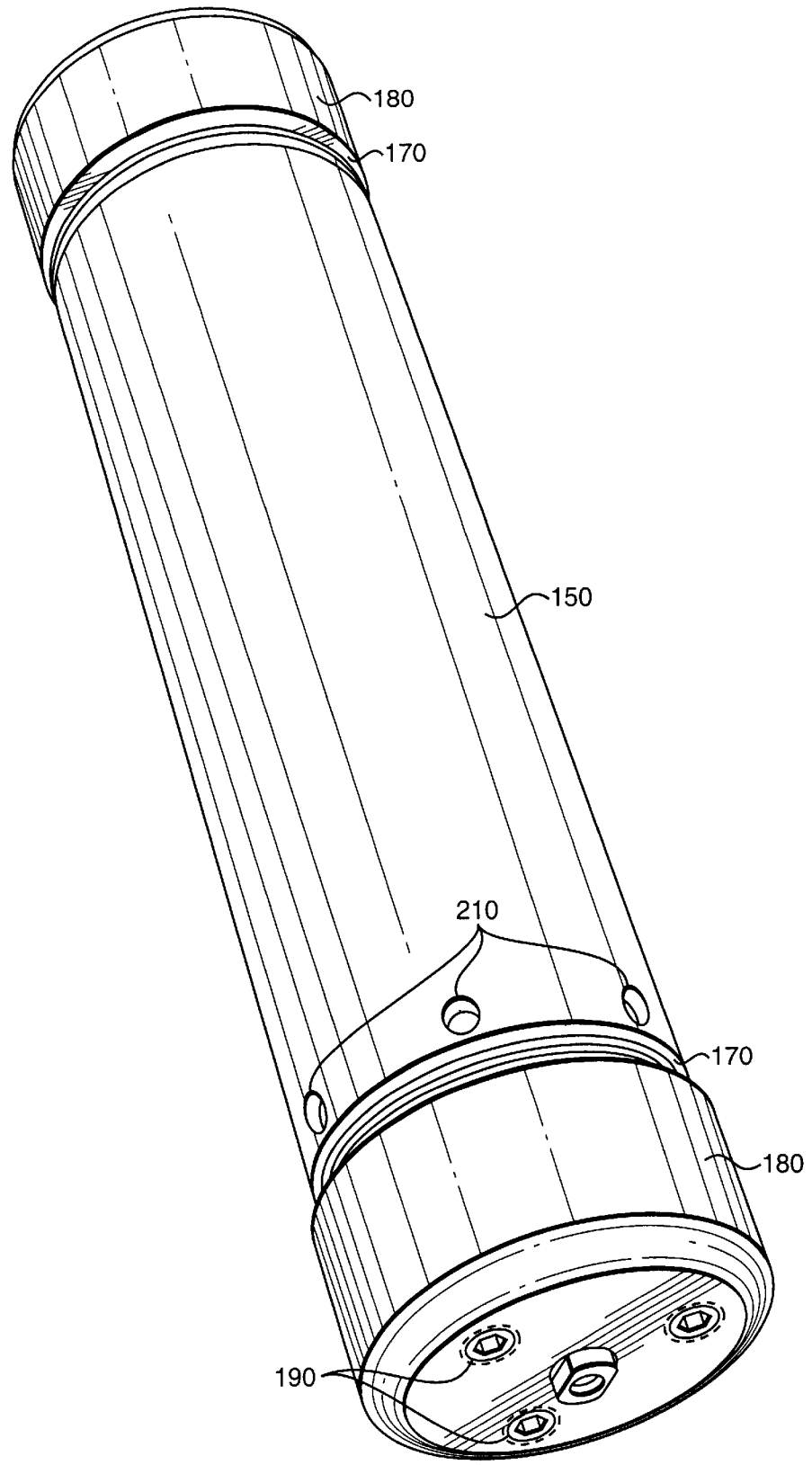
FIG. 3 is a side view of a chromatography column according to the present invention.

Before the chromatography column of the present invention can be used in a chromatography application, it must be filled with packing material, closed, and then attached to a chromatography system. After filling, the following steps are taken to close one end of the chromatography column. First, the filter housing 170 is placed on the end face of the column body 150. Second, the end cap 180 is screwed on to the threaded portion of the column body 150 over the filter housing 170. Third, the mechanical fasteners 200 are tightened. The mechanical fasteners 200 press the filter housing 170 against the end of the column body 150 to effectively seal the chromatography column. The face portion of the filter housing 170 abutting the end of the column body is configured with a sealing member (not shown), such as an O-ring or gasket. FIG. 3 shows a closed chromatography column according to the present invention.

When it becomes necessary to open the chromatography column, for example because the blocked filters must be replaced, the ends of the chromatography column are opened in two simple steps. First, the mechanical fasteners 200 are loosened. Because the mechanical fasteners 200 have small diameters, they are easy to loosen. Loosening the mechanical fasteners 200 releases the tension between the end cap 180 and the threaded portion 160 of the column body 150. Second, the end cap 180 is unscrewed from the column body 150. The torque required to unscrew the loosened end cap 180 can be produced by the hands of an average person.

Small round indentations 210 provide a means for holding the chromatography column while a person is applying torque to loosen the fasteners. The same indentations 210 are used to rotate column with a spanner wrench when connecting it to a packing station.

Although the column in the illustrative embodiment described herein includes an integrated filter and distributor member, it should be appreciated that a filter and/or distributor member could be separately implemented with a sealing end member against which the tension release fasteners could be engaged.

It should be appreciated that although a plurality of mechanical fasteners are used in the tension release mechanism, other mechanical fastening implementation could be effected, such as by using biased locking levers, screws, cams, small diameter bolts or the like.

Although the illustrative embodiment described herein has two removable, substantially identical end portions, it should be appreciated that only one end could be implemented as described, e.g. with a tension release mechanism according to the invention, while the second end has an alternative e.g. non-tension release, implementation.

Although the present invention has been shown and described with respect to illustrative embodiments thereof, various other changes, omissions and additions in the form and detail thereof may be made therein without departing from the spirit and scope of the invention.

What is claimed is:

1. A chromatography column comprising:

a column body, said column body generally cylindrical in shape and having two open ends, said column body defining a chamber for retaining a chromatography medium, at least one end of said column body having an element for receiving an end cap and a cooperating sealing surface for receiving a sealing surface of a filter housing;

at least one filter housing disposed at the end of said column body for retaining a chromatography medium within the chamber, said filter housing has an opening and channeling means for directing fluid to the opening and sealing means to seal said member to said column body;

at least one end cap, said end cap having means for engaging said connecting element of said column body and removable upon rotation, said end cap has a plurality of opening for receiving rods, said plurality of opening having a smaller opening than open end of said column body, said rods having reliably secured to said opening and having at least one end abutting said filter housing to engage said filter housing in a sealing engagement with said column body sealing surface.

2. The chromatography column according to claim 1 wherein the connecting element on said column body receives said end cap which has a means for engaging the connecting element and said end cap.

3. The chromatography column according to claim 1 wherein said end cap openings and rods have cooperating threads.

4. In a liquid chromatography system, a chromatography column comprising:

a column body with at least one threaded end portion;

at least one filter and distributor member disposed on the end portion of said column body;

at least one threaded end cap configured to screw on and off of said column body;

a plurality of holes disposed in said at least one end cap; and a plurality of mechanical fasteners configured for installing into said plurality of holes, providing a tension release mechanism for releasing tension between threads of the threaded end portion and threads of at least one said threaded end cap created when chromatography medium exerts pressure on said at least one filter and distributor member during operation or packaging of the medium in the column body.

5. A chromatography column according to claim 4 wherein said at least one end cap contains three holes.

6. A chromatography column according to claim 4 where the mechanical fasteners are small diameter bolts.

7. A chromatography column according to claim 4 wherein said column body contains a plurality of small round indentations to facilitate holding the column.

8. A chromatography column according to claim 7 wherein the plurality of small round indentations in said column body are used to connect the chromatography column to a parking station while the chromatography column is being packed.

9. A chromatography column according to claim 7 wherein the plurality of small round indentations in said column body are used to hold the chromatography column while a person applies torque to open the column.

10. A chromatography column according to claim 4 wherein said column body has a diameter of at least 50 mm.

11. A chromatography column according to claim 4 wherein said column body is made of stainless steel.

* * * * *